United States Patent
Imagawa et al.

(10) Patent No.: US 10,508,173 B2
(45) Date of Patent: Dec. 17, 2019

(54) COMPOSITION FOR OPTICAL MATERIAL AND OPTICAL MATERIAL USING THE SAME

(71) Applicant: MITSUBISHI GAS CHEMICAL COMPANY, INC., Tokyo (JP)

(72) Inventors: Yousuke Imagawa, Tokyo (JP); Akinobu Horita, Tokyo (JP); Yoshiaki Yamamoto, Tokyo (JP); Hiroshi Horikoshi, Tokyo (JP)

(73) Assignee: MITSUBISHI GAS CHEMICAL COMPANY, INC., Tokyo (JP)

( * ) Notice: Subject to any disclaimer, the term of this patent is extended or adjusted under 35 U.S.C. 154(b) by 88 days.

(21) Appl. No.: 15/566,838

(22) PCT Filed: Jun. 10, 2016

(86) PCT No.: PCT/JP2016/067317
§ 371 (c)(1),
(2) Date: Oct. 16, 2017

(87) PCT Pub. No.: WO2016/204080
PCT Pub. Date: Dec. 22, 2016

(65) Prior Publication Data
US 2018/0127549 A1    May 10, 2018

(30) Foreign Application Priority Data

Jun. 17, 2015 (JP) ................ 2015-122036
Dec. 10, 2015 (JP) ................ 2015-241479

(51) Int. Cl.
| | | |
|---|---|---|
| G02B 1/11 | (2015.01) |
| G02B 1/14 | (2015.01) |
| C08G 75/08 | (2006.01) |
| C08G 75/14 | (2006.01) |
| C07D 331/02 | (2006.01) |
| C07D 341/00 | (2006.01) |

(52) U.S. Cl.
CPC ........... *C08G 75/08* (2013.01); *C07D 331/02* (2013.01); *C07D 341/00* (2013.01); *G02B 1/11* (2013.01); *G02B 1/14* (2015.01)

(58) Field of Classification Search
USPC ....................................................... 428/419
See application file for complete search history.

(56) References Cited

U.S. PATENT DOCUMENTS 3,631,158 A * 12/1971 Esclamadon et al. ......................
                                                                       C01B 17/0243
                                                                         528/377
5,807,975 A      9/1998    Amagai et al.
9,522,879 B2 * 12/2016    Jang ....................... C07C 319/14
2004/0024165 A1    2/2004    Yoshimura et al.
2007/0149639 A1 * 6/2007    Horikoshi ............. C08G 75/08
                                                                         523/102
2010/0331515 A1    12/2010    Takeuchi et al.
2016/0152774 A1    6/2016    Namiki et al.

FOREIGN PATENT DOCUMENTS

| JP | 9-110979 | | 4/1997 |
|---|---|---|---|
| JP | 2002-40201 | | 2/2002 |
| JP | 2002040201 | * | 2/2002 |
| JP | 2002-90502 | | 3/2002 |
| JP | 2004-175726 | | 6/2004 |
| WO | 2014/208656 A1 | | 12/2014 |

OTHER PUBLICATIONS

Machine translated JP 2002-040201, Part 1, Feb. 6, 2002, Japan, 18 pages.*
Machine translated JP 2002-040201, Part 2, Feb. 6, 2002, Japan, 5 pages.*
InternationalSearch Report issued in Patent Application No. PCT/JP2016/067317, dated Sep. 13, 2016.
European Search Report issued with respect to Application No. 16811554.1, dated Jan. 21, 2019.

* cited by examiner

*Primary Examiner* — Tae H Yoon
(74) *Attorney, Agent, or Firm* — Greenblum & Bernstein, P.L.C.

(57) ABSTRACT

The present invention provides a composition for an optical material containing a ring compound (a) represented by formula (1), an episulfide compound (b), and sulfur (c), wherein the content of the ring compound (a) in the composition for an optical material is in the range of 5-70 mass %, the content of the episulfide compound (b) is in the range of 20-90 mass %, and the content of the sulfur (c) is in the range of 1-39 mass %. (In the formula, X represents S, Se or Te. a to f=0 to 3, 8≥(a+c+e)≥1, 8≥(b+d+f)≥2, and (b+d+f)≥(a+c+e).) This composition for an optical material has a high refractive index as an optical characteristic, and has sufficient heat resistance and good mold release characteristics.

(1)

$$\begin{array}{c} H \\ \diagup \\ H-(C)_a-(X)_b\,H \\ \diagup \quad \diagdown\diagup \\ (X)_f \qquad (C)_c \\ \diagdown \quad \diagup\diagdown \\ H-(C)_e-(X)_d\,H \\ \diagdown \\ H \end{array}$$

11 Claims, No Drawings

COMPOSITION FOR OPTICAL MATERIAL AND OPTICAL MATERIAL USING THE SAME

This application is a U.S. national stage application of PCT/JP2016/067317, filed Jun. 10, 2016, which claims priority to Japanese Application No. 2015-241479 filed Dec. 10, 2015, and Japanese Application No. 2015-122036 filed Jun. 17, 2015. The entire disclosure of PCT/JP2016/067317 is incorporated by reference herein.

TECHNICAL FIELD

The present invention relates to a composition for optical materials, etc., and particularly relates to a composition for optical materials, etc. suitable for an optical material for a plastic lens, a prism, an optical fiber, an information recording substrate, a filter or the like, in particular for a plastic lens.

BACKGROUND ART

Plastic lenses are lightweight, highly tough and easy to be dyed. Properties particularly required for plastic lenses are: low specific gravity; high transparency; low yellowness; high refractive index and high Abbe number as optical properties; high heat resistance; high strength; and the like. A high refractive index allows a lens to be thinner, and a high Abbe number reduces the chromatic aberration of a lens.

Recently, many optical materials using an organic compound having a sulfur atom for providing a high refractive index and a high Abbe number have been reported.

Among such optical materials, polyepisulfide compounds having a sulfur atom are known to provide a good balance between the refractive index and the Abbe number (Patent Document 1). High refractive indexes of 1.7 or higher were achieved by optical materials obtained from these polyepisulfide compounds. However, it has been desired to provide a material having a higher refractive index, and an optical material obtained by using a composition for optical materials containing an organic compound having a cyclic skeleton containing a sulfur, selenium or tellurium atom was proposed. Such ring compounds have a refractive index of 1.73 or higher (Patent Document 2).

However, in the case of such optical materials obtained by using a composition for optical materials having a high refractive index, heat resistance may be insufficient, mold release characteristics may be insufficient, and lenses may be easily broken at the time of demolding, and these are the problems.

PRIOR ART DOCUMENTS

Patent Documents

Patent Document 1: Japanese Laid-Open Patent Publication No. H09-110979
Patent Document 2: Japanese Laid-Open Patent Publication No. 2002-040201

SUMMARY OF THE INVENTION

Problems to be Solved by the Invention

The problem to be solved by the present invention is to provide a composition for optical materials, which has a high refractive index and good mold release characteristics, wherein sufficient heat resistance is ensured in an optical material obtained by using the composition for optical materials, and an optical material using the same.

Means for Solving the Problems

The present inventors diligently made researches in order to solve the problem, and found that heat resistance and mold release characteristics of an optical material can be improved by polymerizing and curing a composition for optical materials having a specific composition containing a ring compound (a), an episulfide compound (b) and sulfur (c), and thus the present invention was achieved.

Specifically, the present invention is as described below.
[1] A composition for optical materials containing a ring compound (a) represented by formula (1) below, an episulfide compound (b) and sulfur (c), wherein in the composition for optical materials, the content of the ring compound (a) is 5 to 70% by mass, the content of the episulfide compound (b) is 20 to 90% by mass and the content of the sulfur (c) is 1 to 39% by mass:

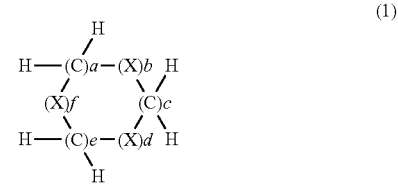

wherein: X represents S, Se or Te; a to f each independently represent an integer of 0 to 3; $8 \geq (a+c+e) \geq 1$; $8 \geq (b+d+f) \geq 2$; and $(b+d+f) \geq (a+c+e)$.
[2] The composition for optical materials according to item [1], wherein in the composition for optical materials, the total content of the ring compound (a) and the episulfide compound (b) is 60 to 99% by mass.
[3] The composition for optical materials according to item [1] or [2], wherein the mass ratio between the ring compound (a) and the episulfide compound (b) ((a)/(b)) is 10/90 to 70/30.
[4] The composition for optical materials according to any one of items [1] to [3], which further contains a thiol compound (d) in an amount of 0.1 to 15 parts by mass relative to 100 parts by mass of the total amount of the ring compound (a), the episulfide compound (b) and the sulfur (c).
[5] The composition for optical materials according to any one of items [1] to [4], wherein in formula (1), X is S.
[6] The composition for optical materials according to any one of items [1] to [5], wherein the ring compound (a) is at least one substance selected from the group consisting of 1,2-dithietane, trithietane, 1,2-dithiolane, 1,2,3-trithiolane, 1,2,4-trithiolane, tetrathiolane, 1,2-dithiane, 1,2,3-trithiane, 1,2,4-trithiane, 1,3,5-trithiane, 1,2,3,4-tetrathiane, 1,2,4,5-tetrathiane, pentathiane, 1,2,3-trithiepane, 1,2,4-trithiepane, 1,2,5-trithiepane, 1,2,3,4-tetrathiepane, 1,2,3,5-tetrathiepane, 1,2,4,5-tetrathiepane, 1,2,4,6-tetrathiepane, 1,2,3,4,5-pentathiepane, 1,2,3,4,6-pentathiepane, 1,2,3,5,6-pentathiepane and hexathiepane.
[7] The composition for optical materials according to any one of items [1] to [6], wherein the episulfide compound (b) is represented by formula (2) below:

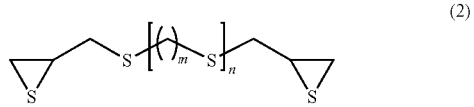

(2)

wherein: m represents an integer of 0 to 4; and n represents an integer of 0 to 2.

[8] The composition for optical materials according to item [4], wherein the thiol compound (d) is at least one substance selected from the group consisting of methanedithiol, 1,2-ethanedithiol, (sulfanylmethyldisulfanyl)methanethiol, bis(2-mercaptoethyl) sulfide, 2,5-bis(mercaptomethyl)-1,4-dithiane, 1,2-bis(2-mercaptoethylthio)-3-mercaptopropane, 4,8-dimercaptomethyl-1,11-dimercapto-3,6,9-trithiaundecane, 4,7-dimercaptomethyl-1,11-dimercapto-3,6,9-trithiaundecane, 5,7-dimercaptomethyl-1,11-dimercapto-3,6,9-trithiaundecane, 1,2,6,7-tetramercapto-4-thiaheptane, tetramercaptopentaerythritol, 1,3-bis(mercaptomethyl)benzene and thiiranemethanethiol.

[9] The composition for optical materials according to any one of items [1] to [8], wherein 0.0001 to 10% by mass of a polymerization catalyst is contained in the composition for optical materials.

[10] A resin obtained by curing the composition for optical materials according to any one of items [1] to [9].

[11] An optical material obtained by using the resin according to item [10].

[12] The optical material according to item [11], which further has a hard coat layer having a refractive index of 1.67 or higher.

[13] The optical material according to item [12], which further has an antireflection film.

Advantageous Effect of the Invention

An optical material obtained by using the composition for optical materials of the present invention has sufficient heat resistance and mold release characteristics, and therefore it is possible to provide a high-performance optical material.

BEST MODE FOR CARRYING OUT THE INVENTION

Hereinafter, the present invention will be described in detail. The scope of the present invention is not limited to the description. In addition to the following examples, the present invention can be suitably changed and then practiced within a range in which the effects of the present invention are not reduced. Note that all the documents and publications cited herein are incorporated herein by reference in their entireties regardless of purposes thereof. In addition, the contents disclosed in the claims and specifications of Japanese Patent Application No. 2015-122036 (filed on Jun. 17, 2015) and Japanese Patent Application No. 2015-241479 (filed on Dec. 10, 2015), to which priority is claimed by the present application, are incorporated herein.

The composition for optical materials of the present invention contains a ring compound (a), an episulfide compound (b) and sulfur (c). Essential components of the composition for optical materials of the present invention are the ring compound (a), the episulfide compound (b) and the sulfur (c), but it is preferred to add a thiol compound (d), a curing catalyst and at least one of various additives according to need.

Hereinafter, the ring compound (a), the episulfide compound (b), the sulfur (c) and compounds that can be added as a composition for optical materials, which are raw materials to be used in the present invention, will be described in detail.

The ring compound (a) to be used in the present invention has a structure represented by formula (1) below.

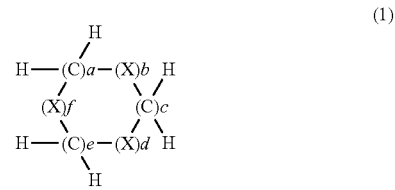

(1)

(In the formula: X represents S, Se or Te; a to f each independently represent an integer of 0 to 3; $8 \geq (a+c+e) \geq 1$; $8 \geq (b+d+f) \geq 2$; and $(b+d+f) \geq (a+c+e)$.)

Regarding the aforementioned compound (a), X in formula (1) is S, Se or Te, and in terms of availability and toxicity, it is preferably S or Se, and more preferably S.

a to f each independently represent an integer of 0 to 3, $8 \geq (a+c+e) \geq 1$, and $8 \geq (b+d+f) \geq 2$. In terms of ready availability and providing a composition having a high refractive index, preferably, $8 \geq (a+c+e) \geq 1$ and $7 \geq (b+d+f) \geq 2$, and more preferably, $5 \geq (a+c+e) \geq 1$ and $7 \geq (b+d+f) \geq 2$. Even more preferred is a compound further satisfying $(b+d+f) \geq (a+c+e)$.

Further, for obtaining a high refractive index, the total of S, Se and Te in the ring compound (a) is preferably 50% by mass or more.

Specific examples of the ring compound (a) include, but are not limited to, dithiirane, 1,2-dithietane, 1,3-dithietane, trithietane, 1,2-dithiolane, 1,3-dithiolane, 1,2,3-trithiolane, 1,2,4-trithiolane, tetrathiolane, 1,2-dithiane, 1,3-dithiane, 1,4-dithiane, 1,2,3-trithiane, 1,2,4-trithiane, 1,3,5-trithiane, 1,2,3,4-tetrathiane, 1,2,4,5-tetrathiane, 1,3-dithiepane, 1,4-dithiepane, 1,2,3-trithiepane, 1,2,4-trithiepane, 1,2,5-trithiepane, 1,3,5-trithiepane, 1,2,3,4-tetrathiepane, 1,2,3,5-tetrathiepane, 1,2,4,5-tetrathiepane, 1,2,4,6-tetrathiepane, 1,2,3,4,5-pentathiepane, 1,2,3,4,6-pentathiepane, 1,2,3,5,6-pentathiepane, hexathiepane, diselecyclobutane, triselecyclobutane, diselecyclopentane, triselecyclopentane, tetraselecyclopentane, diselecyclohexane, triselecyclohexane, tetraselecyclohexane, pentaselecyclohexane, diselecycloheptane, triselecycloheptane, tetraselecycloheptane, pentaselecycloheptane, hexaselecycloheptane, ditellurocyclobutane, tritellurocyclobutane, ditellurocyclopentane, tritellurocyclopentane, tetratellurocyclopentane, ditellurocyclohexane, tritellurocyclohexane, tetratellurocyclohexane, pentatellurocyclohexane, ditellurocycloheptane, tritellurocycloheptane, tetratellurocycloheptane, pentatellurocycloheptane, hexatellurocycloheptane and derivatives thereof having a cyclic skeleton structure (compounds in which hydrogen atom(s) are substituted with any of various substituents).

Preferred specific examples thereof include 1,2-dithietane, trithietane, 1,2-dithiolane, 1,2,3-trithiolane, 1,2,4-trithiolane, tetrathiolane, 1,2-dithiane, 1,2,3-trithiane, 1,2,4-trithiane, 1,3,5-trithiane, 1,2,3,4-tetrathiane, 1,2,4,5-tetrathiane, pentathiane, 1,2,3-trithiepane, 1,2,4-trithiepane, 1,2,5-trithiepane, 1,2,3,4-tetrathiepane, 1,2,3,5-tetrathiepane, 1,2,4,5-tetrathiepane, 1,2,4,6-tetrathiepane, 1,2,3,4,5-pentathiepane, 1,2,3,4,6-pentathiepane, 1,2,3,5,6-pentathiepane, hexathiepane and derivatives thereof having a cyclic skeleton structure (in which hydrogen atom(s) are substituted with any of various substituents), because these substances can be easily obtained or synthesized and a composition having a high refractive index can be obtained by using them. Particularly preferred are 1,2,4,5-tetrathiane and 1,2,3,5,6-pentathiepane.

As the ring compound (a), these substances may be used solely, or two or more of them may be used as a mixture.

The method for obtaining the ring compound (a) is not particularly limited. A commercially-available product may be used as the ring compound (a). Alternatively, the ring compound (a) may be collected and extracted from natural products such as crude oil, animals and plants or may be synthesized according to a publicly-known method.

Examples of synthesis methods include those of: N. Takeda et al., Bull. Chem. Soc. Jpn., 68, 2757 (1995); F. Feher et al., Angew. Chem. Int. Ed., 7, 301 (1968); and G. W. Kutney et al., Can. J. Chem, 58, 1233 (1980).

The content of the ring compound (a) in the composition for optical materials (100% by mass) is 5 to 70% by mass, preferably 5 to 50% by mass, and more preferably 10 to 40% by mass.

When the content of the ring compound (a) is less than 5% by mass, the effect of improving the refractive index may not be sufficiently obtained. When the content is more than 70% by mass, transparency of an optical material obtained may be deteriorated.

The episulfide compound (b) to be used in the present invention includes all episulfide compounds. In terms of heat resistance, it is preferably a compound having two episulfide groups in the molecule.

Hereinafter, specific examples of the episulfide compound (b) are classified into a compound having a chain aliphatic skeleton, a compound having an aliphatic cyclic skeleton and a compound having an aromatic skeleton and listed below, but the episulfide compound (b) is not limited thereto.

Examples of the compound having a chain aliphatic skeleton include a compound represented by formula (2) below.

(2)

(In the formula, m represents an integer of 0 to 4, and n represents an integer of 0 to 2.)

Specific examples thereof include bis(β-epithiopropyl) sulfide (n=0 in formula (2) above), bis(β-epithiopropyl) disulfide (m=0 and n=1 in formula (2) above), bis(β-epithiopropylthio)methane (m=1 and n=1 in formula (2) above), 1,2-bis(β-epithiopropylthio)ethane (m=2 and n=1 in formula (2) above), 1,3-bis(β-epithiopropylthio)propane (m=3 and n=1 in formula (2) above), 1,4-bis(β-epithiopropylthio)butane (m=4 and n=1 in formula (2) above) and bis(β-epithiopropylthioethyl)sulfide (m=2 and n=2 in formula (2) above).

Examples of the compound having an aliphatic cyclic skeleton include a compound represented by formula (3) or (4) below.

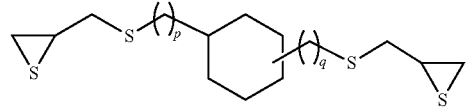

(3)

(In the formula, p and q each independently represent an integer of 0 to 4.)

Specific examples of the compound represented by formula (3) include 1,3- and 1,4-bis(β-epithiopropylthio)cyclohexane (p=0 and q=0 in formula (3) above) and 1,3- and 1,4-bis(β-epithiopropylthiomethyl)cyclohexane (p=1 and q=1 in formula (3) above).

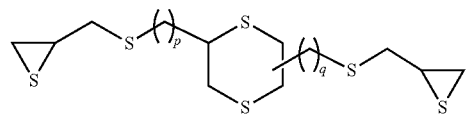

(4)

(In the formula, p and q each independently represent an integer of 0 to 4.)

Specific examples of the compound represented by formula (4) include 2,5-bis(β-epithiopropylthio)-1,4-dithiane (p=0 and q=0 in formula (4) above) and 2,5-bis(β-epithiopropylthioethylthiomethyl)-1,4-dithiane (p=1 and q=1 in formula (4) above).

Examples of the compound having an aromatic skeleton include a compound represented by formula (5), (6) or (7) below.

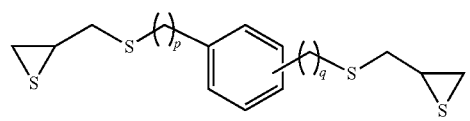

(5)

(In the formula, p and q each independently represent an integer of 0 to 4.)

Specific examples of the compound represented by formula (5) include 1,3- and 1,4-bis(β-epithiopropylthio)benzene (p=0 and q=0 in formula (5) above) and 1,3- and 1,4-bis(β-epithioproplythiomethyl)benzene (p=1 and q=1 in formula (5) above).

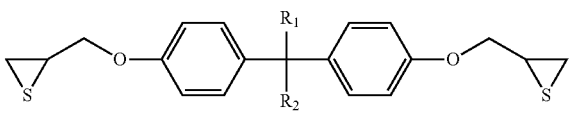

(6)

(In the formula, $R_1$ and $R_2$ each independently represent H, Me (methyl), Et (ethyl) or Ph (phenyl).)

Specific examples of the compound represented by formula (6) include a bisphenol F-type episulfide compound in which both $R_1$ and $R_2$ are H and a bisphenol A-type episulfide compound in which both $R_1$ and $R_2$ are Me.

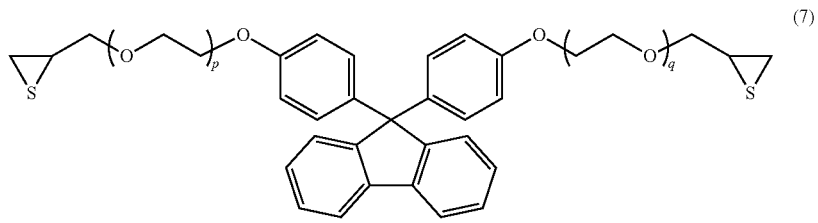

(In the formula, p and q each independently represent an integer of 0 or 1.)

Specific examples of the compound represented by formula (7) include a compound, wherein p=0 and q=0 in formula (7) above, and a compound, wherein p=1 and q=1 in formula (7) above.

As the episulfide compound (b), these substances may be used solely, or two or more of them may be used as a mixture.

In terms of availability, the compound having a chain aliphatic skeleton represented by formula (2) above is preferred, and bis(β-epithiopropyl)sulfide (n=0 in formula (1) above) and bis(β-epithiopropyl)disulfide (m=0 and n=1 in formula (1) above) are particularly preferred.

The method for obtaining the episulfide compound (b) is not particularly limited. A commercially-available product may be used as the episulfide compound (b). Alternatively, the episulfide compound (b) may be synthesized according to a publicly-known method. For example, bis(β-epithiopropyl)sulfide (n=0 in formula (1) above) can be synthesized according to a publicly-known technique (Japanese Patent No. 3491660).

The content of the episulfide compound (b) in 100% by mass of the composition for optical materials is 20 to 90% by mass, preferably 20 to 70% by mass, and more preferably 30 to 70% by mass.

This is because, when the content of the episulfide compound (b) is 20% by mass or less, a reaction thereof with the ring compound (a) is insufficient, and when the content is more than 90% by mass, the refractive index is reduced.

The sulfur (c) to be used in the present invention means an elemental sulfur in which S8 sulfur is a unit structure, and a commercially-available product can be easily obtained as the sulfur (c).

The sulfur to be used in the present invention may be in any form. Specifically, the sulfur is finely-powdered sulfur, colloidal sulfur, precipitated sulfur, crystalline sulfur, sublimed sulfur or the like, and is preferably finely-powdered sulfur having fine particles.

The content of the sulfur (c) in the composition for optical materials is 1 to 39% by mass, and in terms of heat resistance and mold release characteristics, the content is preferably 5 to 35% by mass, and more preferably 15 to 30% by mass. In terms of further improvement of heat resistance, the content is even more preferably 20 to 30% by mass.

Note that when the content of the sulfur (c) less than 1% by mass, the improvement of heat resistance and mold release characteristics as the effects of the present invention cannot be achieved, and when the content is more than 39% by mass, the sulfur is not completely reacted, resulting in precipitation of the solid.

The sulfur (c) may be mixed directly as the composition for optical materials, but for efficiently obtaining an optical material, preferably, the sulfur (c) is preliminarily reacted with the episulfide compound (b) in advance.

When performing a preliminary reaction, conditions thereof are −10° C. to 120° C. and 0.1 to 240 hours, preferably 0 to 100° C. and 0.1 to 120 hours, and particularly preferably 20 to 80° C. and 0.1 to 60 hours.

Further, for promoting the preliminary reaction, a catalyst for preliminary reaction can be used and it is effective.

Examples of the catalyst for preliminary reaction include 2-mercapto-1-methylimidazole, triphenylphosphine, 3,5-dimethylpyrazole, N-cyclohexyl-2-benzothiazolylsulfinamide, dipentamethylene thiuramtetrasulfide, tetrabutyl thiuram disulfide, tetraethyl thiuram disulfide, 1,2,3-triphenylguanidine, 1,3-diphenylguanidine, 1,1,3,3-tetramethyleneguanidine, aminoguanidineurea, trimethylthiourea, tetraethylthiourea, dimethylethylthiourea, zinc dibutyldithiocarbamate, zinc dibenzyldithiocarbamate, zinc diethyldithiocarbamate, zinc dimethyldithiocarbamate and pipecorium pipecolyldithiocarbamate.

For suppressing precipitation of solid sulfur, it is preferred that 10% or more of the sulfur is consumed by this preliminary polymerization reaction (when the amount of the whole sulfur before the reaction is regarded as 100%), and it is more preferred that 20% or more of the sulfur is consumed thereby.

The preliminary reaction may be performed in any atmosphere, for example, under inert gas such as air, nitrogen or the like, in a sealed state under normal pressure or raised or reduced pressure, or the like. In order to detect how much the preliminary reaction has proceeded, liquid chromatography or a refractometer can be used.

The composition for optical materials of the present invention can be prepared by mixing the ring compound (a), the episulfide compound (b) and the sulfur (c), and a compound which is added according to need.

Firstly, the contents of the ring compound (a), the episulfide compound (b) and the sulfur (c) in the composition for optical materials will be described.

In the composition for optical materials (100% by mass): the content of the ring compound (a) is 5 to 70% by mass, preferably 5 to 50% by mass, and more preferably 10 to 40% by mass; the content of the episulfide compound (b) is 20 to 90% by mass, preferably 20 to 70% by mass, and more preferably 30 to 70% by mass; and the content of the sulfur (c) is 1 to 39% by mass, preferably 5 to 35% by mass, more preferably 15 to 30% by mass, and even more preferably 20 to 30% by mass.

Further, in terms of color tone, the total content of the ring compound (a) and the episulfide compound (b) in the composition for optical materials (100% by mass) is preferably 60 to 99% by mass, more preferably 65 to 90% by mass, and even more preferably 70 to 86% by mass.

Regarding the preferred ratio between the ring compound (a) and the episulfide compound (b), the mass ratio between the ring compound (a) and the episulfide compound (b) ((a)/(b)) is 10/90 to 70/30. This is because, when the composition for optical materials is within the above-described range, good balanced and suitable physical properties can be obtained in terms of heat resistance, refractive index and transparency. In terms of further improvement of heat resistance, the mass ratio is more preferably 20/80 to 60/40, and even more preferably 20/80 to 40/60.

Further, in the present invention, a thiol compound (d) can be added to the composition for optical materials for the purpose of providing good color phase of the optical material. The thiol compound is a polymerizable compound containing at least one thiol group in the molecule. The thiol compound may have at least one episulfide group in addition to the at least one thiol group. Note that the above-described "episulfide compound (b)" does not include any compound containing a thiol group.

The thiol compound (d) to be used in the present invention includes all thiol compounds. Preferred are a polymerizable compound (polythiol compound) containing at least two thiol groups in the molecule and a polymerizable compound containing at least one thiol group and at least one episulfide group in the molecule.

In terms of availability, preferred specific examples of the compound include methanedithiol, 1,2-ethanedithiol, (sulfanylmethyldisulfanyl)methanethiol, bis(2-mercaptoethyl) sulfide, 2,5-bis(mercaptomethyl)-1,4-dithiane, 1,2-bis(2-mercaptoethylthio)-3-mercaptopropane, 4,8-dimercaptomethyl-1,11-dimercapto-3,6,9-trithiaundecane, 4,7-dimercaptomethyl-1,11-dimercapto-3,6,9-trithiaundecane, 5,7-dimercaptomethyl-1,11-dimercapto-3,6,9-trithiaundecane, 1,1,3,3-tetrakis(mercaptomethylthio)propane, 1,2,6,7-tetramercapto-4-thiaheptane, tetramercaptopentaerythritol, 1,3-bis(mercaptomethyl)benzene, 1,4-bis(mercaptomethyl)benzene and thiiranemethanethiol, and more preferred specific examples of the compound include methanedithiol, 1,2-ethanedithiol, (sulfanylmethyldisulfanyl)methanethiol, bis (2-mercaptoethyl) sulfide, 2,5-bis(mercaptomethyl)-1,4-dithiane, 1,2-bis(2-mercaptoethylthio)-3-mercaptopropane, 4,8-dimercaptomethyl-1,11-dimercapto-3,6,9-trithiaundecane, 4,7-dimercaptomethyl-1,11-dimercapto-3,6,9-trithiaundecane, 5,7-dimercaptomethyl-1,11-dimercapto-3,6,9-trithiaundecane, 1,2,6,7-tetramercapto-4-thiaheptane, tetramercaptopentaerythritol, 1,3-bis(mercaptomethyl)benzene and thiiranemethanethiol.

As the thiol compound, these substances may be used solely, or two or more of them may be used as a mixture.

In the present invention, the amount of the thiol compound (d) to be added is preferably 0.1 to 15 parts by mass relative to 100 parts by mass of the total of the ring compound (a), the episulfide compound (b) and the sulfur (c). This is because, when the amount is less than 0.1 parts by mass, color tone may be deteriorated, and when the amount is more than 10 parts by mass, surfaces of lenses may become rough. In terms of light resistance, the amount of the thiol compound (d) to be added is more preferably 0.5 to 12 parts by mass, and particularly preferably 1 to 10 parts by mass. According to such a preferred embodiment, it is possible to obtain a composition for optical materials which has sufficient heat resistance and mold release characteristics as well as good light resistance, and it is possible to provide an optical material with higher performances. The optical material of the embodiment, which has excellent light resistance, can be particularly suitably used in the case where use environment is always exposed to light, for example, for spectacle lenses.

For the production of the optical material of the present invention, various additives such as a curing catalyst, a modifier (various performance modifiers), an antioxidant, a blueing agent, an ultraviolet absorber and a mold release agent can be further added according to need.

Examples of the curing catalyst include amines, phosphines, quaternary ammonium salts, quaternary phosphonium salts, tertiary sulfonium salts, secondary iodonium salts, mineral acids, Lewis acids, organic acids, silicic acids, tetrafluoroborates, peroxides, azo-based compounds, a condensation product of aldehyde with an ammonia-based compound, guanidines, thioureas, thiazoles, sulfenamides, thiurams, dithiocarbamates, xanthogenates and acidic phosphoric acid esters. Preferred are amines, phosphines, quaternary ammonium salts and quaternary phosphonium salts, and more preferred are quaternary ammonium salts and quaternary phosphonium salts. Specific examples of more preferred curing catalysts include quaternary ammonium salts such as tetra-n-butylammonium bromide, triethylbenzyl ammonium chloride, cetyldimethylbenzyl ammonium chloride and 1-n-dodecyl pyridinium chloride and quaternary phosphonium salts such as tetra-n-butylphosphonium bromide and tetraphenyl phosphonium bromide. Among them, even more preferred polymerization catalysts are tetra-n-butylammonium bromide, triethylbenzyl ammonium chloride and tetra-n-butylphosphonium bromide.

In the present invention, the amount of the curing catalyst to be added is preferably 0.0001 to 10.0 parts by mass relative to 100 parts by mass of the composition for optical materials (the total of the composition excluding the curing catalyst). That is, one embodiment of the present invention is a polymerizable and curable composition containing a polymerization catalyst in an amount of 0.0001% by mass to 10% by mass relative to the total amount of the composition for optical materials. The amount of the curing catalyst is more preferably 0.0005 to 5.0 parts by mass. When the amount of the polymerization catalyst to be added is more than 5 parts by mass, the refractive index and heat resistance of a cured product may be reduced and coloring may occur. When the amount is less than 0.001 parts by mass, curing may be performed insufficiently and heat resistance may be insufficient.

As the modifier, epoxy compounds, isocyanates, etc. can be added for the purpose of the improvement of various performances such as oxidation resistance, weather resistance, dyeability, strength and refractive index of the composition (composition for optical materials or polymerizable and curable composition). In the present invention, the amount of the modifier to be added is determined within a range in which optical physical properties and mechanical physical properties are not impaired and cannot be determined unambiguously because of the chemical structure thereof, etc., but it is preferably 10 parts by mass or less relative to 100 parts by mass of the composition for optical materials.

Further, amounts of the antioxidant, the blueing agent, the ultraviolet absorber, etc. to be added are not particularly limited and determined within a range in which optical physical properties and mechanical physical properties are not impaired. For example, these adding amounts are 10 parts by mass or less relative to 100 parts by mass of the composition for optical materials.

Hereinafter, specific examples of the method for producing an optical material in the present invention will be described.

The ring compound (a), the episulfide compound (b), the sulfur (c), and according to need, the thiol compound (d) and additives such as the curing catalyst, the antioxidant, the blueing agent, the ultraviolet absorber and the modifier (various performance modifiers) are homogeneously mixed to prepare a composition (composition for optical materials or polymerizable and curable composition). After that, the composition is injected into a mold made of glass or metal, a polymerization and curing reaction is promoted by heating, and then the obtained product is released from the mold, thereby producing a resin obtained by curing the composition for optical materials or polymerizable and curable composition. The obtained molded body of thermosetting resin can be suitably used as an optical material.

The composition (composition for optical materials or polymerizable and curable composition) of the present invention is usually polymerized (cured) by heating as described below. Specifically, the curing time is usually 1 to 100 hours, and the curing temperature is usually −10° C. to 140° C. The polymerization is conducted by carrying out a step of retaining the composition at a predetermined polymerization temperature for a predetermined amount of time, a step of increasing the temperature at a rate of 0.1° C. to 100° C./h and a step of decreasing the temperature at a rate of 0.1° C. to 100° C./h, or a combination of these steps. Note that the curing time means the time for polymerization and curing including the elevated temperature process, etc., and in addition to the step of retaining the composition at a predetermined polymerization (curing) temperature, steps of increasing/decreasing the temperature to a predetermined polymerization (curing) temperature are included.

Note that it is also possible to preliminarily polymerize a part or all of components of the composition (composition for optical materials or polymerizable and curable composition) at −100 to 160° C. over 0.1 to 480 hours prior to cast molding in the presence or absence of a catalyst for preliminary reaction with or without stirring to subsequently prepare the composition (composition for optical materials or polymerizable and curable composition), followed by cast molding.

Particularly when a solid content is contained in compounds in the composition (composition for optical materials or polymerizable and curable composition) and this causes difficulty in handling, this preliminary polymerization is effective. Conditions for the preliminary polymerization are preferably −10 to 120° C. and 0.1 to 240 hours, and more preferably 0 to 100° C. and 0.1 to 120 hours.

Moreover, after curing is completed, the optical material obtained in the present invention may be subjected to a surface treatment such as dyeing, hard coating, impact-resistant coating, antireflection treatment and imparting antifog properties according to need.

The dyeing method is not particularly limited, and examples thereof include the method described in Japanese Laid-Open Patent Publication No. H04-93310. Usually, dyeing is performed in a dye bath at about room temperature to about 200° C. A desired temperature may not be obtained by usual heating depending on a bath component. In this case, pressurization is performed or a component by which the boiling point can be elevated is added, and according to the so-called ebullioscopic method, a desired dyeing temperature is realized.

In the case where the boiling point is elevated by pressurization, dyeing is usually performed under 1.1 to 20 atmospheric pressure using a pressure vessel, autoclave or the like. As a boiling point elevation component, when the bath component is water, usually an inorganic salt and a water-soluble organic compound, which exert the effect of molar elevation of boiling point, can be added. The inorganic salt to be used is not limited as long as it is a general water-soluble inorganic substance typified by calcium chloride, potassium iodide, etc. The water-soluble organic compound to be used is not limited as long as it is a general water-soluble organic substance typified by urea, sodium acetate, etc.

Regarding the optical material obtained in the present invention (that is, the molded body of thermosetting resin obtained above), a hard coat layer can be provided to at least one surface of the molded body. As the hard coat layer to be used in the present invention, a conventionally-known hard coat layer for plastic lenses can be used. A hard coating solution in which a resin sensitive to active energy ray or a photocurable resin is dissolved or dispersed is applied onto a plastic substrate, it is heated and/or irradiated with active energy ray for curing, thereby forming the hard coat layer. As the active energy ray, ultraviolet light, infrared light, visible light, X-ray and radiation can be used, but in general, ultraviolet light is often used. Specific examples of ultraviolet curable resins include (meth)acrylic resin, urethane acrylate resin, epoxy acrylate resin, unsaturated polyester resin, phosphazene resin, melamine resin and acrylic silane resin.

As a hard coat forming component, a publicly-known thermosetting resin, photocurable resin or the like can be used.

Specific examples of the hard coat layer using the thermosetting resin include those using a melamine-based resin, silicone-based resin, urethane-based resin, acrylic resin or the like, but in terms of light resistance and heat resistance, a hard coat using a silicone-based resin is most preferred. As one specific example, a coating composition consisting of metal oxide fine particles and a silane compound is applied and cured to provide a hard coat layer. This coating composition may contain components including colloidal silica, a polyfunctional epoxy compound, etc.

Specific examples of the photocurable resin include (meth)acrylic resin, urethane acrylate resin, epoxy acrylate resin, unsaturated polyester resin, phosphazene resin, melamine resin and acrylic silane-based resin. For promoting curing of the hard coat forming component, a publicly-known thermal and/or active energy ray polymerization initiator can be added according to need. The amount thereof to be added is usually 0.001 to 10 parts by mass, and preferably 0.01 to 5 parts by mass relative to 100 parts by mass of the hard coat forming component used. For the purpose of adjusting the refractive index for suppressing interference fringes and improving surface hardness, fine particles can be added to the hard coat solution. As the fine particles, metal oxide fine particles are mainly and suitably used, and specifically, zinc oxide, aluminium oxide, silicon dioxide, titanium oxide, zirconium oxide, tin oxide, beryllium oxide, germanium oxide, antimony oxide, tungsten oxide, cerium oxide, etc. can be used. These metal oxide fine particles can be used solely, or two or more of them can be used as a mixture. Two or more of them in a composite state or solid solution state can also be used.

Moreover, the hard coat layer to be used in the present invention may contain conventionally-known various additives. The hard coat layer may contain various leveling agents for improving coatability, an ultraviolet absorber and an antioxidant for improving weather resistance, and additives such as a dye and a pigment.

The hard coat solution may be applied by dipping or using an application apparatus such as a hand coater, a bar coater, a roll coater, a spin coater and a sprayer according to need. The hard coat solution is preferably handled in a clean environment such as a clean room in order to avoid contamination including dust and foreign matter. It is preferred to perform filtration treatment in advance using a filter of PTFE, PET or the like in terms of attaining high transparency of an obtained optical material subjected to hard coating. Further, curing may be performed under a stream of an inert gas such as nitrogen and helium while suitably covering with a film or the like. When heating is used in combination with thermal curing or active energy ray curing, usually, the curing temperature of the hard coat solution is preferably room temperature to 200° C., and more preferably room temperature to 150° C. When the curing temperature is within the above-described range, sufficient effects can be obtained, and coat crack, yellowing of a plastic substrate and a hard coat, etc. can be avoided, and therefore it is preferred.

The refractive index of the hard coat is preferably 1.67 or higher. This is because, when the difference between the refractive index of the substrate and that of the hard coat later is large, it may cause generation of interference fringes.

Regarding the optical material obtained in the present invention, an antireflection film can be formed on the hard coat layer according to need. It is known that the antireflection film may be either a single layer or a multilayer. As a material for a high refractive index, $TiO_2$, $ZrO_2$, $Ta_2O_5$, etc. are mainly used, and as a material for a low refractive index, $SiO_2$, etc. are used. In the most common constitution, the above-described material for a high refractive index and material for a low refractive index are laminated alternately. These materials are laminated alternately according to the vacuum deposition method, ion-assisted deposition method or the like, thereby forming the antireflection film.

An antifog layer and a water-repellent layer can be further formed on the antireflection film according to need. Regarding the formation of an antifog layer, for example, a method of forming a hydrophilic film to improve water absorbability and a method of providing a water-repellent coating are known. Further, regarding the formation of a water-repellent layer, a method of applying a fluorine-containing silane compound and a method of forming a film of a fluorine-containing silane compound by means of deposition, sputtering or the like are known.

As described above, the composition for optical materials of the present invention can provide an optical material having a high refractive index and excellent heat resistance and mold release characteristics. Thus, the optical material (molded body; cured product; cured resin) obtained by curing the above-described composition (composition for optical materials or polymerizable and curable composition) is also one embodiment of the present invention.

The refractive index is preferably 1.5 or higher, more preferably 1.70 or higher, and even more preferably 1.75 or higher. The refractive index can be measured by a refractometer, and is a value obtained by the measurement at 25° C. and at a wavelength of 546.1 nm (e-line).

Regarding heat resistance of the optical material, the softening point at the time of increasing the temperature of the optical material is preferably 50° C. or higher, and more preferably 70° C. or higher.

The optical material of the present invention is useful for various applications including, for example, optical members, materials for machine parts, materials for electric and electronic parts, materials for automotive parts, materials for civil engineering and construction, molding materials and materials for paints and adhesives. The optical material is particularly suitable for: optical applications such as lenses including spectacle lenses, imaging lenses for (digital) cameras, light beam condensing lenses and light diffusing lenses, sealants for LEDs, adhesives for optical applications, bonding materials for optical transmission, optical fibers, prisms, filters, diffraction gratings, watch glasses, and transparent glasses or cover glasses including cover glasses for display devices; display device applications such as coating agents (coating films) for substrates for display elements including LCD, organic EL and PDP, substrates for color filters, substrates for touch panels, information recording substrates, display backlights, light guide plates, display protection films, antireflection films, antifog films, etc.; and the like. As the above-described optical material, particularly, an optical material for an optical lens, a prism, an optical fiber, an information recording substrate, a filter or the like, in particular an optical lens is suitable.

An optical lens produced by using the composition for optical materials of the present invention has excellent stability, color phase, transparency, etc., and therefore can be used in the field in which expensive glass lenses having a high refractive index have been conventionally used including telescopes, binoculars and television projectors and is very useful. The optical lens is preferably used in the form of an aspherical lens according to need.

EXAMPLES

Hereinafter, the present invention will be specifically described by way of examples. However, the present invention is not limited to these examples, and embodiments can be suitably changed within a range in which the effects of the present invention are exerted.

Note that lenses obtained were evaluated in manners described below.
[Refractive Index of Optical Material]
Regarding the refractive index of the optical material, the refractive index at the e-line (wavelength: 546.1 nm) at 25° C. was measured using a digital precision refractometer (Shimadzu Corporation, KPR-200).
[Measurement of Heat Resistance (Tg) of Optical Material]
A sample was cut to have a thickness of 3 mm, and the TMA measurement (Seiko Instruments Inc., TMA/SS6100) was carried out by adding 10 g of weight to a pin (φ: 0.5 mm) and elevating the temperature from 30° C. at a rate of 10° C./min to measure the softening point. The case where the softening point was 70° C. or higher was rated as A. The case where the softening point was 50° C. or higher and lower than 70° C. was rated as B. The case where the softening point was lower than 50° C. was rated as C. A and B are regarded as acceptable.
[Mold Release Characteristics]
10 lenses of −4 D having a diameter of 70 mm and a central thicknesses of 1.0 mm were prepared, and mold release characteristics thereof were evaluated. The case where 10 lenses were successfully removed from the mold was rated as A. The case where 9 lenses were successfully removed from the mold was rated as B. The case where 8 lenses were successfully removed from the mold was rated as C. The case where 7 lenses or less were successfully removed from the mold was rated as D. A, B and C are regarded as acceptable.
[Light Resistance]
Lenses having a thickness of 2.5 mm were irradiated with Weather-Ometer Ci4000 (manufactured by ATLAS) for 24 hours at an irradiance of 60 W/m², at a black panel temperature of 65° C. and at a relative humidity of 50%, wherein Type S was used for an inside filter of a lamp and Type S was used for an outside filter. After that, the YI value of each lens was measured. The amount of increase of the YI value when compared to that before irradiation is referred to as the δYI value. The case where the δYI value was less than 6 was rated as A. The case where the δYI value was 6 or more and less than 8 was rated as B. The case where the δYI value was 8 or more was rated as C.

Synthesis Example 1

1,2,3,5,6-pentathiepane was synthesized in the procedure described below according to the method described in the document (H. C. Hansen et al., Tetrahedron, 41, 5145 (1985)).

In a reaction flask equipped with a stirring machine, a dropping funnel and a thermometer, 1.33 mol (146.6 g) of sodium disulfide was mixed with 1000 ml of ethanol under nitrogen stream. 1000 ml of ethanol solution containing 1.35 mol (102.8 g) of carbon bisulfide was added dropwise thereto over 20 minutes with the temperature being kept at 35 to 40° C. using ice bath, and it was stirred at this temperature for 2 hours.

It was confirmed that the reaction solution became a reddish orange suspension. After that, 1.50 mol (409.5 g) of diiodomethane was added dropwise thereto over 20 minutes, and it was further stirred for 2 hours. It was confirmed that the reaction solution became a pale yellow suspension, and the reaction was finished.

After the reaction, extraction was carried out using diethyl ether, water washing was carried out, and the solvent was distilled away, thereby obtaining a product in a yellow liquid state. The product was purified by silica gel column chromatography using hexane as an eluting solvent, thereby obtaining 10.6 g of a solid product.

It was confirmed that the product was 1,2,3,5,6-pentathiepane from the melting point (61 to 62° C.) and results of mass spectrometry, NMR analysis and IR analysis.

Synthesis Example 2

1,2,4,5-tetrathiane was synthesized in the procedure described below according to the method described in the document (Mahabir Parshad Kaushik et al., Chemistry Letters, 35, 1048 (2006)).

In a reaction flask equipped with a stirring machine, 1.00 mol (80.16 g) of methanedithiol, 1000 ml of methylene chloride and 0.05 mol (5.45 g) of silica chloride were stirred under oxygen atmosphere at 0° C. for 10 minutes. After the reaction, extraction was carried out using diethyl ether, water washing was carried out, and the solvent was distilled away, thereby obtaining a product in a yellow liquid state. The product was purified by silica gel column chromatography using hexane as an eluting solvent, thereby obtaining 70.3 g of a solid product.

It was confirmed that the product was 1,2,4,5-tetrathiane from the melting point (67 to 68° C.) and results of mass spectrometry, NMR analysis and IR analysis.

Example 1

To 14 parts by mass of 1,2,3,5,6-pentathiepane obtained in Synthesis Example 1 as the ring compound (a) (hereinafter referred to as "the compound (a-1)"), 56 parts by mass of bis(β-epithiopropyl)sulfide as the episulfide compound (b) (hereinafter referred to as "the compound (b-1)") and 30 parts by mass of sulfur (finely-powdered sulfur) (c), tetra-n-butylammonium bromide as the curing catalyst was added in an amount of 0.2 parts by mass relative to 100 parts by mass of the total of the aforementioned components, and the mixture was stirred at 60° C. to obtain a homogenous solution. Next, it was filtered with a PTFE filter of 0.5 μm, injected into a mold for lenses of −4 D having a diameter of 70 mm and a central thicknesses of 1.0 mm, and polymerized and cured in an oven with the temperature being elevated from 10° C. to 120° C. over 22 hours, thereby producing lenses. The measurement results of the refractive index, heat resistance and light resistance and mold release characteristics of the obtained lenses are shown in Table 1.

Examples 2-4

The process was carried out in a manner similar to that in Example 1, except that the composition was as shown in Table 1. The measurement results of the refractive index, heat resistance and light resistance and mold release characteristics of the lenses are shown in Table 1.

Example 5

The process was carried out in a manner similar to that in Example 1, except that as the thiol compound (d), 1,2-dimercaptoethane (hereinafter referred to as "the compound (d-1)") was used and the composition was as shown in Table 1. The measurement results of the refractive index, heat resistance and light resistance and mold release characteristics of the lenses are shown in Table 1.

Example 6

The process was carried out in a manner similar to that in Example 1, except that as the thiol compound (d), 1,3-bis(mercaptomethyl)benzene (hereinafter referred to as "the compound (d-2)") was used and the composition was as shown in Table 1. The measurement results of the refractive index, heat resistance and light resistance and mold release characteristics of the lenses are shown in Table 1.

Example 7

The process was carried out in a manner similar to that in Example 1, except that as the thiol compound (d), 1,2-bis(2-mercaptoethylthio)-3-mercaptopropane (hereinafter referred to as "the compound (d-3)") was used and the composition was as shown in Table 1. The measurement results of the refractive index, heat resistance and light resistance and mold release characteristics of the lenses are shown in Table 1.

Example 8

The process was carried out in a manner similar to that in Example 1, except that the composition was as shown in Table 1. The measurement results of the refractive index, heat resistance and light resistance and mold release characteristics of the lenses are shown in Table 1.

Example 9

The process was carried out in a manner similar to that in Example 1, except that the composition was as shown in Table 1. The measurement results of the refractive index, heat resistance and light resistance and mold release characteristics of the lenses are shown in Table 1.

Example 10

The process was carried out in a manner similar to that in Example 1, except that as the thiol compound (d), methanedithiol (hereinafter referred to as "the compound (d-4)") was used and the composition was as shown in Table 1. The measurement results of the refractive index, heat resistance and light resistance and mold release characteristics of the lenses are shown in Table 1.

Example 11

The process was carried out in a manner similar to that in Example 1, except that as the thiol compound (d), (sulfanylmethyldisulfanyl)methanethiol (hereinafter referred to as "the compound (d-5)") was used and the composition was as shown in Table 1. The measurement results of the refractive index, heat resistance and light resistance and mold release characteristics of the lenses are shown in Table 1.

Example 12

The process was carried out in a manner similar to that in Example 1, except that as the thiol compound (d), bis(2-mercaptoethyl) sulfide (hereinafter referred to as "the compound (d-6)") was used and the composition was as shown in Table 1. The measurement results of the refractive index, heat resistance and light resistance and mold release characteristics of the lenses are shown in Table 1.

Example 13

The process was carried out in a manner similar to that in Example 1, except that as the thiol compound (d), 1,2,6,7-tetramercapto-4-thiaheptane (hereinafter referred to as "the compound (d-7)") was used and the composition was as shown in Table 1. The measurement results of the refractive index, heat resistance and light resistance and mold release characteristics of the lenses are shown in Table 1.

Example 14

The process was carried out in a manner similar to that in Example 1, except that as the thiol compound (d), tetramercaptopentaerythritol (hereinafter referred to as "the compound (d-8)") was used and the composition was as shown in Table 1. The measurement results of the refractive index, heat resistance and light resistance and mold release characteristics of the lenses are shown in Table 1.

Example 15

The process was carried out in a manner similar to that in Example 1, except that as the thiol compound (d), thiiranemethanethiol (hereinafter referred to as "the compound (d-9)") was used and the composition was as shown in Table 1. The measurement results of the refractive index, heat resistance and light resistance and mold release characteristics of the lenses are shown in Table 1.

Example 16

The process was carried out in a manner similar to that in Example 1, except that as the ring compound (a), 1,2,4,5-tetrathiane obtained in Synthesis Example 2 (hereinafter referred to as "the compound (a-2)") was used and the composition was as shown in Table 1. The measurement results of the refractive index, heat resistance and light resistance and mold release characteristics of the lenses are shown in Table 1.

Examples 17-19

The process was carried out in a manner similar to that in Example 13, except that the composition was as shown in Table 1. The measurement results of the refractive index, heat resistance and light resistance and mold release characteristics of the lenses are shown in Table 1.

Comparative Examples 1 and 3

The process was carried out in a manner similar to that in Example 1, except that the composition was as shown in Table 1. The measurement results of the refractive index, heat resistance and light resistance of the lenses are shown in Table 1.

Comparative Example 2

The process was carried out in a manner similar to that in Example 16, except that the composition was as shown in Table 1. The measurement results of the refractive index, heat resistance and light resistance of the lenses are shown in Table 1.

Comparative Example 4

When the mixture having the composition shown in Table 1 was stirred at 60° C. to obtain a homogenous solution and then it was cooled to room temperature, solid sulfur was precipitated.

TABLE 1

| Examples | Ring compound (a) (parts by mass) | Episulfide compound (b) (parts by mass) | Sulfur (c) (parts by mass) | Thiol compound (d) (parts by mass) | (a)/(b) | Refractive index | Heat resistance | Mold release characteristics | Light resistance |
|---|---|---|---|---|---|---|---|---|---|
| Example 1 | a-1 14 | b-1 56 | c 30 | 0 | 20/80 | 1.806 | A | A | C |
| Example 2 | a-1 22.5 | b-1 52.5 | c 25 | 0 | 30/70 | 1.804 | A | A | C |
| Example 3 | a-1 33 | b-1 49.5 | c 17.5 | 0 | 40/60 | 1.797 | B | A | C |
| Example 4 | a-1 32.6 | b-1 48.9 | c 18.5 | 0 | 40/60 | 1.800 | B | A | C |
| Example 5 | a-1 13.3 | b-1 53.2 | c 28.5 | d-1 5 | 20/80 | 1.802 | A | A | A |
| Example 6 | a-1 13.3 | b-1 53.2 | c 28.5 | d-2 5 | 20/80 | 1.798 | B | A | B |
| Example 7 | a-1 13.3 | b-1 53.2 | c 28.5 | d-3 5 | 20/80 | 1.799 | B | A | A |

TABLE 1-continued

Table 1

| Examples | Ring compound (a) (parts by mass) | Episulfide compound (b) (parts by mass) | Sulfur (c) (parts by mass) | Thiol compound (d) (parts by mass) | (a)/(b) | Refractive index | Heat resistance | Mold release characteristics | Light resistance |
|---|---|---|---|---|---|---|---|---|---|
| Example 8 | a-1 15.2 | b-1 60.8 | c 19 | d-2 5 | 20/80 | 1.768 | B | A | B |
| Example 9 | a-1 15.2 | b-1 60.8 | c 19 | d-3 5 | 20/80 | 1.771 | A | A | A |
| Example 10 | a-1 15.2 | b-1 60.8 | c 19 | d-4 5 | 20/80 | 1.767 | B | A | A |
| Example 11 | a-1 15.2 | b-1 60.8 | c 19 | d-5 5 | 20/80 | 1.774 | B | A | A |
| Example 12 | a-1 15.2 | b-1 60.8 | c 19 | d-6 5 | 20/80 | 1.767 | B | A | B |
| Example 13 | a-1 15.2 | b-1 60.8 | c 19 | d-7 5 | 20/80 | 1.770 | B | A | A |
| Example 14 | a-1 15.2 | b-1 60.8 | c 19 | d-8 5 | 20/80 | 1.770 | B | A | A |
| Example 15 | a-1 15.2 | b-1 60.8 | c 19 | d-9 5 | 20/80 | 1.770 | A | A | B |
| Example 16 | a-2 14 | b-1 56 | c 30 | 0 | 20/80 | 1.803 | A | B | C |
| Example 17 | a-1 25.4 | b-1 51.5 | c 21.6 | d-7 1.5 | 33/67 | 1.796 | A | A | B |
| Example 18 | a-1 24.7 | b-1 50 | c 22.3 | d-7 3 | 33/67 | 1.796 | B | A | A |
| Example 19 | a-1 23.9 | b-1 48.5 | c 22.6 | d-7 5 | 33/67 | 1.770 | B | A | A |
| Comparative Example 1 | a-1 70 | b-1 30 | c 0 | 0 | 70/30 | 1.798 | C | D | C |
| Comparative Example 2 | a-2 70 | b-1 30 | c 0 | 0 | 70/30 | 1.795 | C | D | C |
| Comparative Example 3 | a-1 39.8 | b-1 59.7 | c 0.5 | 0 | 40/60 | 1.758 | C | D | C |
| Comparative Example 4 | a-1 24 | b-1 36 | c 40 | 0 | 40/60 | Solid precipitation | | | |

From Table 1 above, it is confirmed that when using a composition for optical materials containing a ring compound (a), an episulfide compound (b) and sulfur (c) in predetermined amounts, an optical material having excellent heat resistance and mold release characteristics is obtained with a high refractive index being maintained.

Meanwhile, it is confirmed that heat resistance and mold release characteristics are poor in Comparative Examples 1 and 2 in which sulfur (c) was not contained and Comparative Example 3 in which the content of sulfur (c) was small.

Further, in Comparative Example 4 in which the content of sulfur (c) was large, sulfur was precipitated, and therefore it is difficult to use the composition as an optical material.

Moreover, from Table 1 above, it is confirmed that when using a composition for optical materials further containing a thiol compound (d) in a predetermined amount (Examples 5-15 and 17-19), an optical material further having excellent light resistance in addition to excellent heat resistance and mold release characteristics is obtained. Such an optical material further having excellent light resistance can be particularly suitably used in the case where use environment is always exposed to light, for example, for spectacle lenses.

The invention claimed is:

1. A composition for optical materials containing
a ring compound (a) that is at least one substance selected from the group consisting of dithiirane, 1,2-dithietane, 1,3-dithietane, trithietane, 1,2,3-trithiolane, 1,2,4-trithiolane, tetrathiolane, 1,2,3-trithiane, 1,2,4-trithiane, 1,2,3,4-tetrathiane, 1,2,4,5-tetrathiane, 1,2,3,4-tetrathiepane, 1,2,3,5-tetrathiepane, 1,2,4,5-tetrathiepane, 1,2,4,6-tetrathiepane, 1,2,3,4,5-pentathiepane, 1,2,3,4,6-pentathiepane, 1,2,3,5,6-pentathiepane, hexathiepane, diselecyclobutane, triselecyclobutane, triselecyclopentane, tetraselecyclopentane, diselecyclohexane, tetraselecyclohexane, pentaselecyclohexane, tetraselecycloheptane, pentaselecycloheptane, hexaselecycloheptane, ditellurocyclobutane, tritellurocyclobutane, tritellurocyclopentane, tetratellurocyclopentane, tetratellurocyclohexane, pentatellurocyclohexane, tetratellurocycloheptane, pentatellurocycloheptane, and hexatellurocycloheptane,
an episulfide compound (b),
sulfur (c), and
a thiol compound (d) that is at least one substance selected from the group consisting of methanedithiol, 1,2-ethanedithiol, (sulfanylmethyldisulfanyl)methanethiol, bis (2-mercaptoethyl) sulfide, 2,5-bis(mercaptomethyl)-1,4-dithiane, 1,2-bis(2-mercaptoethylthio)-3-mercaptopropane, 4,8-dimercaptomethyl-1,11-dimercapto-3,6,9-trithiaundecane, 4,7-dimercaptomethyl-1,11-dimercapto-3,6,9-trithiaundecane, 5,7-dimercaptomethyl-1,11-dimercapto-3,6,9-trithiaundecane, 1,2,6,7-tetramercapto-4-thiaheptane, tetramercaptopentaerythritol, 1,3-bis(mercaptomethyl) benzene, and thiiranemethanethiol,
wherein in the composition for optical materials, the content of the ring compound (a) is 5 to 70% by mass, the content of the episulfide compound (b) is 20 to 90% by mass, the content of the sulfur (c) is 1 to 39% by mass, and the thiol compound (d) is 0.1 to 15 parts by mass relative to 100 parts by mass of the total amount of the ring compound (a), the episulfide compound (b), and the sulfur (c).

2. The composition for optical materials according to claim 1, wherein in the composition for optical materials, the total content of the ring compound (a) and the episulfide compound (b) is 60 to 99% by mass.

3. The composition for optical materials according to claim 1, wherein the mass ratio between the ring compound (a) and the episulfide compound (b) ((a)/(b)) is 10/90 to 70/30.

4. The composition for optical materials according to claim 1, wherein the ring compound (a) is at least one substance selected from the group consisting of 1,2-dithietane, trithietane, 1,2,3-trithiolane, 1,2,4-trithiolane, tetrathiolane, 1,2,3-trithiane, 1,2,4-trithiane, 1,2,3,4-tetrathiane, 1,2,4,5-tetrathiane, pentathiane, 1,2,3,4-tetrathiepane, 1,2,3,5-tetrathiepane, 1,2,4,5-tetrathiepane, 1,2,4,6-tetrathiepane, 1,2,3,4,5-pentathiepane, 1,2,3,4,6-pentathiepane, 1,2,3,5,6-pentathiepane, and hexathiepane.

5. The composition for optical materials according to claim 1, wherein the episulfide compound (b) is represented by formula (2) below:

(2)

wherein: m represents an integer of 0 to 4; and n represents an integer of 0 to 2.

6. A polymerizable and curable composition, which contains: the composition for optical materials according to claim 1; and a polymerization catalyst in an amount of 0.0001 to 10% by mass relative to the total amount of the composition for optical materials.

7. A resin obtained by curing the composition for optical materials according to claim 1.

8. An optical material obtained by using the resin according to claim 7.

9. The optical material according to claim 8, which further has a hard coat layer having a refractive index of 1.67 or higher.

10. The optical material according to claim 9, which further has an antireflection film.

11. A resin obtained by curing the polymerizable and curable composition according to claim 6.

* * * * *